United States Patent
Heijman et al.

(10) Patent No.: US 9,851,708 B2
(45) Date of Patent: Dec. 26, 2017

(54) SENSOR FOR MOVING EQUIPMENT

(71) Applicant: KONINKLIJKE PHILIPS N.V., Eindhoven (NL)

(72) Inventors: Edwin Heijman, Eindhoven (NL); Roland Alexander Van De Molengraaf, Geldrop (NL); Marc Matysek, Hofheim (DE)

(73) Assignee: Koninklijke Philips N.V., Eindhoven (NL)

( * ) Notice: Subject to any disclaimer, the term of this patent is extended or adjusted under 35 U.S.C. 154(b) by 231 days.

(21) Appl. No.: 14/439,345

(22) PCT Filed: Oct. 25, 2013

(86) PCT No.: PCT/IB2013/059660
§ 371 (c)(1),
(2) Date: Apr. 29, 2015

(87) PCT Pub. No.: WO2014/072869
PCT Pub. Date: May 15, 2014

(65) Prior Publication Data
US 2015/0277420 A1     Oct. 1, 2015

Related U.S. Application Data

(60) Provisional application No. 61/722,858, filed on Nov. 6, 2012.

(51) Int. Cl.
*H02P 7/00*     (2016.01)
*G05B 19/19*    (2006.01)
(Continued)

(52) U.S. Cl.
CPC .............. *G05B 19/19* (2013.01); *A61B 6/467* (2013.01); *G06F 3/044* (2013.01); *H03K 17/962* (2013.01);
(Continued)

(58) Field of Classification Search
CPC .......... G05B 19/19; G05B 2219/43162; F04C 2270/041; A61B 6/467; A61B 6/102;
(Continued)

(56) References Cited

U.S. PATENT DOCUMENTS

| 4,492,949 A | * | 1/1985 | Peterson | ................ B25J 13/084 |
| | | | | 338/114 |
| 5,339,350 A | * | 8/1994 | Thelosen | ............. A61B 6/4405 |
| | | | | 378/194 |

(Continued)

FOREIGN PATENT DOCUMENTS

| CN | 102743187 A | 10/2012 |
| DE | 102012002604 A1 | 2/2011 |

(Continued)

OTHER PUBLICATIONS

Nagakubo, A. et al. "A deformable and deformation sensitive tactile distribution sensor". Robotics and Biomimetics, 2007, p. 1301-1308, Publisher: IEEE.

*Primary Examiner* — Rita Leykin

(57) ABSTRACT

The present invention relates to a moving equipment, such as in a medical examination system. In order to provide a facilitated way of moving equipment with high accuracy, a driving device (10) for moving equipment is provided, comprising a motor-driven positioning unit (12), a central processing unit (14), and a user interface (16) with at least one sensor unit (18). The motor-driven positioning unit is configured to carry out a movement (M) of movable equipment. Further, the central processing unit is configured to control the movement of the equipment provided by the motor-driven positioning unit. The at least one sensor unit comprises at least one touch sensitive area (20), and the at least one sensor unit is configured to provide control signals (22) to the central processing unit in dependency from a force (F) applied by a user to the at least one touch sensitive (Continued)

area. Still further, the at least one sensor unit is configured to be fixedly attached to the movable equipment.

18 Claims, 6 Drawing Sheets

(51) Int. Cl.
| | |
|---|---|
| H03K 17/96 | (2006.01) |
| H03K 17/975 | (2006.01) |
| G06F 3/044 | (2006.01) |
| A61B 6/04 | (2006.01) |
| A61B 6/10 | (2006.01) |
| A61B 6/00 | (2006.01) |
| G01D 5/241 | (2006.01) |

(52) U.S. Cl.
CPC .......... *H03K 17/975* (2013.01); *A61B 6/0457* (2013.01); *A61B 6/102* (2013.01); *A61B 6/4441* (2013.01); *F04C 2270/041* (2013.01); *G01D 5/2417* (2013.01); *G05B 2219/43162* (2013.01); *H03K 2017/9602* (2013.01); *H03K 2217/96062* (2013.01)

(58) Field of Classification Search
CPC ..... A61B 6/4441; A61B 6/0457; G06F 3/044; H03K 17/962; H03K 17/975; H03K 2017/9602; H03K 2017/9605; H03K 2217/96062; G01D 5/2417
USPC ..... 318/290, 649; 378/195, 208; 324/755.08
See application file for complete search history.

(56) References Cited

U.S. PATENT DOCUMENTS

| | | | | | |
|---|---|---|---|---|---|
| 5,561,699 | A * | 10/1996 | Fenner | ................. | A61B 6/0457 378/204 |
| 6,045,262 | A * | 4/2000 | Igeta | .................... | A61B 6/0457 318/649 |
| 6,072,130 | A * | 6/2000 | Burgess | ................. | H01H 1/029 200/86 R |
| 7,034,432 | B1 * | 4/2006 | Pelrine | .................... | F02G 1/043 310/309 |
| 7,160,027 | B2 * | 1/2007 | Bauer | ................... | A61B 6/4482 318/2 |
| 7,567,681 | B2 * | 7/2009 | Pelrine | ...................... | B64C 3/48 381/176 |
| 7,658,119 | B2 * | 2/2010 | Loeb | ...................... | B25J 13/084 73/862.046 |
| 7,685,886 | B2 * | 3/2010 | Sano | .................... | A61B 5/0053 73/849 |
| 7,878,075 | B2 * | 2/2011 | Johansson | .............. | B25J 13/084 73/862.046 |
| 8,409,173 | B2 * | 4/2013 | Brown | ................. | H03K 17/962 600/102 |
| 8,419,717 | B2 * | 4/2013 | Diolaiti | .................. | G05B 19/19 606/1 |
| 8,529,128 | B2 * | 9/2013 | Horiuchi | .............. | A61B 6/4482 378/196 |
| 8,797,271 | B2 * | 8/2014 | Kramer | .............. | G06F 3/04883 178/18.01 |
| 8,915,151 | B2 * | 12/2014 | Choi | ...................... | H01H 13/85 200/330 |
| 9,349,552 | B2 * | 5/2016 | Huska | ..................... | G06F 3/016 |
| 9,381,645 | B1 * | 7/2016 | Yarlagadda | ............ | G05B 19/42 |
| 9,569,079 | B2 * | 2/2017 | Kramer | .............. | G06F 3/04883 |
| 2002/0130673 | A1 * | 9/2002 | Pelrine | .................. | A63H 3/365 324/727 |
| 2007/0227267 | A1 * | 10/2007 | Loeb | ...................... | B25J 13/084 73/862.046 |
| 2008/0130836 | A1 | 6/2008 | Graumann | | |
| 2008/0194909 | A1 | 8/2008 | Brown | | |
| 2009/0015270 | A1 * | 1/2009 | Hayakawa | .............. | G01L 1/142 324/686 |
| 2009/0022275 | A1 * | 1/2009 | Grebner | ................. | A61B 6/467 378/95 |
| 2009/0120696 | A1 * | 5/2009 | Hayakawa | .............. | G01L 1/205 178/18.05 |
| 2009/0189873 | A1 * | 7/2009 | Peterson | ................. | G06F 3/016 345/173 |
| 2010/0033196 | A1 * | 2/2010 | Hayakawa | ............... | G01B 7/22 324/686 |
| 2010/0164324 | A1 * | 7/2010 | Kim | ........................ | H01G 5/16 310/318 |
| 2010/0193341 | A1 * | 8/2010 | Uotani | .................. | G06F 3/0338 200/5 A |
| 2011/0227872 | A1 * | 9/2011 | Huska | .................... | G06F 3/016 345/174 |
| 2012/0126959 | A1 * | 5/2012 | Zarrabi | .................... | B06B 1/0688 340/407.1 |

FOREIGN PATENT DOCUMENTS

| | | |
|---|---|---|
| KR | 20110130891 A | 12/2011 |
| WO | 2008052561 A1 | 5/2008 |

* cited by examiner

SENSOR FOR MOVING EQUIPMENT

CROSS-REFERENCE TO PRIOR APPLICATIONS

This application is the U.S. National Phase application under 35 U.S.C. §371 of International Application Serial No. PCT/IB2013/059660, filed on Oct. 25, 2013, which claims the benefit of U.S. Application Ser. No. 61/722,858, filed on Nov. 6, 2012. These applications are hereby incorporated by reference herein.

FIELD OF THE INVENTION

The present invention relates to a driving device for moving equipment, a medical examination system, to a sensor of a touch sensitive area for detecting a direction of an actuating force, and to a method for moving equipment, as well as to a computer program element, and to a computer-readable medium.

BACKGROUND OF THE INVENTION

For moving objects, for example for moving medical equipment in an examination room, such as a medical imaging system or a patient table, the base structures can be equipped with wheels in order to roll the equipment manually across the floor or the base structure consists of a mechanical structure, fixed to a wall or ceiling or device, to move the equipment in space. Further, equipment can be provided with motor-driven wheels for a mechanical movement, for example controlled by an interface such as a joystick or switches. The manual movement of equipment is cumbersome in particular in case of rather heavy components that need to be moved. U.S. Pat. No. 5,339,350 describes a movable X-ray apparatus with a steering handle. Further, it has been shown that movement control by joysticks or the like requires a certain experience with such interfaces for a correct and accurate movement of the equipment.

SUMMARY OF THE INVENTION

There may be a need to provide a facilitated way of moving equipment with high accuracy.

The object of the present invention is solved by the subject-matter of the independent claims, wherein further embodiments are incorporated in the dependent claims. It should be noted that the following described aspects of the invention apply also for the driving device for moving equipment, the medical examination system, the sensor of a touch sensitive area for detecting a direction of an actuating force and the method for moving equipment, as well as to the computer program element, and the computer readable medium.

According to a first aspect of the present invention, a driving device for moving equipment is provided, comprising a motor-driven positioning unit, a central processing unit, and a user interface with at least one sensor unit. The motor-driven positioning unit is configured to carry out a movement of movable equipment. The central processing unit is configured to control the movement of the equipment provided by the motor-driven positioning unit. The at least one sensor unit comprises at least one touch sensitive area, and is configured to provide control signals to the central processing unit in dependency from a force, such as a pressure applied by a user to the at least one touch sensitive area. The at least one sensor unit is configured to be fixedly attached to the movable equipment.

The pressure, i.e. force may be applied perpendicular to the sensor's surface. The pressure may also be provided along the surface as a shear force.

Since the sensor unit is provided to be mounted to movable equipment, the sensor is always available in place, namely directly at the moving equipment itself. Further, since the control signals are provided, or generated, according to the force applied by the user, the user is provided with an intuitive way for moving the equipment. Since the sensor is provided to be fixedly attached to the movable equipment, the sensor itself moves away during the application of a force, e.g. pressure force onto the sensor to provide an accurate and fast feedback loop in form of the well-developed human hand-eye-coordination as the hand is kept close to the sensor unit and thus the input device that is moving in the room, for example. Even though the movement itself is performed and achieved by the movement direction-positioning unit, the user has a similar feeling as if he or she would move the object in a natural way, but with a lower weight. The movement force is provided by the motor-driven positioning unit. Following, any particular skills or experience with special interfaces like a joystick or switches is not required. This makes the above-described driving device in particular suitable for use in environments where any unnecessary attention means a distraction from other tasks, for example in examination laboratories or hospital rooms. The sensor may be covered by a special material on which bacteria cannot grow. The provided movement results in a relative movement of the equipment to the surrounding space and in relation to the user. However, the sensor unit itself moves together with the equipment.

The term "equipment" relates to components and units of different kind. For example, the components and units may comprise movable machines in a craftsman shop, a manufacturing site, or a workshop. The equipment is moved inside the room, for example. Another example is equipment in the medical field, such as a medical imaging apparatus, patient support, patient table, monitoring arrangement, live support machines, and the like.

The term "to move" comprises moving and/or positioning in 3D space, or along a predetermined plane or surface in space, such as on a floor. The term "to move" also comprises moving equipment supported from a ceiling or a wall.

The movement direction-positioning unit may be provided as a motor-supported suspension unit or base structure of equipment. The movement direction-positioning unit may be provided as a motor-supported drive unit for moving at least a part of the equipment.

According to an example, the equipment is a medical apparatus, and the motor-driven positioning unit is configured to carry out a movement of the medical equipment in an examination room.

According to a further example, the sensor unit is configured to provide control signals in dependency from at least one of the group of: i) pressure force, and ii) pressure acting direction.

The terms "force" and e.g. "pressure force" relate to the actuating force by the user acting on the sensor surface. The pressure force may vary when the sensor surface, together with the equipment is moving upon actuation. The term "pressure direction" or "force direction" is the direction, or the resulting vector of the actuating force applied by the user acting on the sensor surface.

For example, if the equipment should be moved in a certain direction across the floor surface, the user has to provide an actuating force or pressure onto the sensor surface in the desired direction. If the movement should take place in a rather speedy manner, the user has to apply the pressure with an increased pressure force in order to speed up the acceleration and thus speed up the movement. Thus, a direct feedback possibility is provided, since an increase of a pressure force, or a decrease, has immediate effect on the movement, which movement is experienced by the user while pressing, i.e. actuating the sensor, since the sensor itself moves together with the equipment. To decelerate the equipment, the user can provide a pressure force in the opposite direction of the motion, or in case of a perpendicular force to the surface sensor lower than a certain threshold.

According to an example, the touch sensitive area is configured to be arranged on the movable equipment such that a force is executable by a user in an acting direction touching the touch sensitive area, which acting direction is in concordance with an intended moving direction.

This allows the user to act on the equipment without having to think about any specific working function of an interface unit such as a joystick and its orientation in space, i.e. in the room.

The intended direction is a moving direction that is carried out while the pressing or actuating force is acting on the touch sensitive area. The term "concordance" relates to an alignment of the actuating, i.e. pressure acting direction and the accomplished moving direction. For example, the intended moving direction is parallel to the acting direction. In another example, the acting direction is the same, or slightly deviating therefrom, as the intended moving direction.

The force or pressure acting direction comprises different vector components that are detectable by the sensor to provide a movement control signal with respective movement vector components.

According to an example, the user interface comprises a haptic feedback unit, which is configured to provide a haptic signal to the user while the user is in touching contact with the sensor unit.

The term "haptic signal" refers to a signal that is experienced by the user with his/her touching sense, for example with the hand, or fingers respectively, and is thus provided as a direct feedback signal in an opposite way of communicating compared to the touching of the sensor unit for actuating the movement or motion of the equipment. Thus, by providing the feedback in the same way of communication between the machine and the user as the way of entering control commands, an intuitive and direct, and thus accurate and fast feedback loop is provided.

According to an example, a collision control unit is provided to detect an upcoming collision of the movable component, wherein the feedback is provided as a haptic warning signal via the touch sensitive area.

In another example, in addition or instead of the haptic feedback signal, an acoustical and/or optical warning signal is provided.

A confirmation unit may be provided to enable and/or block an unwanted operation of the motor drive unit.

According to an example, the touch sensitive area is a deformable capacitive sensor.

For example, a dielectric elastomer or foam, incorporating two or more electrodes, which may overlap, is provided. A dielectric elastomer may also be provided as an actuator for providing feedback. The sensor and the actuator can be integrated in the same "touch area", for example by providing the same electrodes with a layer in-between and switching between a sensing mode and an actuation mode.

In one example of the sensor, different signals are provided that can be used alone or in combination. One signal is the capacity change, and another signal is the voltage change, wherein the voltage may vary for example with $1/A^2$, where A is the surface.

For example, a dielectric polymer is used only as a sensor. The device can operate in a low voltage regime, which is contributing to safety aspects.

In another example, for a haptic feedback provided by the same polymer acting as an actuator, electric fields may be provided in the 10-400 V/$\mu$m range. In another example, a stacked actuator/sensor is provided. The sensor, or the sensor with integrated actuator for feedback may thus be provided a single layer or as stacked design.

In another example, for actuation, compliant electrodes are provided. For example, the electrodes stretch in the same order as the elastomer In an example, the driving device of the examples above is integrated into movable equipment. For example, the motor-driven positioning unit may be integrated into a base structure or support structure of the equipment. The sensor unit with its sensitive area is provided on the outside of the structure such that the user can easily reach the sensor surface for activating the drive mechanism if movement is desired. The surface of the sensor is free in shape.

According to a second aspect, a medical examination system is provided, comprising at least one movable medical equipment of the group of an imaging apparatus, a patient support, and a display. At least one of the medical equipment comprises a movable support and is provided with a driving device according to one of the above-described examples and embodiments. The at least one sensor is attached to the movable medical equipment.

The medical examination system may be provided as a medical imaging system, e.g. an X-ray imaging system, an ultrasound imaging system, an MRT-, MR-, or CT-system for imaging an object of interest, such as a patient. The medical examination system may be provided as a catheterization laboratory. The medical examination system may comprise interventional devices.

According to an example, the imaging apparatus is a C-arm arrangement of a C-arm X-ray imaging system, and sensor surfaces are provided at least on two sides of the X-ray detector or X-ray source.

The sensor surfaces may be provided at least on two sides of the movable medical equipment.

According to an example, the patient support is a patient table, and sensor surfaces are provided at least on one side, for example, on two sides of the patient table.

The sensor surfaces may be provided along the edges. The sensor surfaces may also be provided on handles, or grips, for moving the equipment.

According to an example, the sensor surfaces are provided as large surfaces on the movable medical equipment. The large surfaces are provided with at least one of the group of a length that is at least half way along an edge of the medical equipment, and a length of at least 30 cm, and a surface area of at least 20 cm×20 cm.

According to a third aspect, a sensor of a touch sensitive area for detecting a direction of an actuating force is provided, that comprises a first and a second layer of electrodes and a dielectric elastomer. The first and the second layer are spaced apart by the dielectric elastomer in a variable distance according to a force, e.g. pressure force, acting on the sensor. One of the first or second layers of electrodes comprises at least one electrode that at least partly overlaps with at least two electrodes of the other one of the second or first layer of electrodes. This is provided to uncouple the electrodes from the user's hand, which can also create a capacitive change. A local change of capacity provides information about strain and direction on an acting force.

The actuating force may be a pressing force. Further, in addition or as alternative, a force along the surface, i.e. a shear force, is provided.

For example, one electrode overlaps with three or four electrodes in the opposite layer. In a further example, a plurality of overlapping electrodes arrangements is provided across the touch sensitive area.

In further examples, the driving device according to the before-mentioned example is provided with such sensor as described above.

According to a fourth aspect of the present invention, a method for moving equipment is provided, comprising the following steps:
 a) touching a touch sensitive area of a sensor unit of a user interface, which sensor unit is attached to a movable equipment;
 b) generating a control signal in dependency from a force applied by a user to the at least one touch sensitive area;
 c) providing the generated control signal to a central processing unit; and
 d) actuating a motor-driven positioning unit based on the control signal.

According to an example, a further step is provided, in which the haptic signal is provided to the user while in touching contact with the sensor unit. The haptic signal is provided as a different degree of softness in dependency of the weight of the equipment to be moved.

According to an aspect, a sensor is provided directly on an equipment that should be moved, such as heavy objects of medical systems, in order to enable the user to put his hand, or other body parts, such a hip, a leg, or a shoulder, on the sensor and to exert a pressure as if the object, i.e. the equipment, is moved in a manual manner. The sensor detects the force and controls motors in order to cause a corresponding displacement of the object, i.e. the equipment. Further, a close loop between induced pressure on the sensor and equipment acceleration is provided. The force is amplified making it lighter compared to move heavy equipment. In an example, the pressure is detected. In a further example, the sensor is capable of detecting several directions for, for example, lateral displacements. The sensor surface may be deformable and also responding with haptic signals for a direct user feedback.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
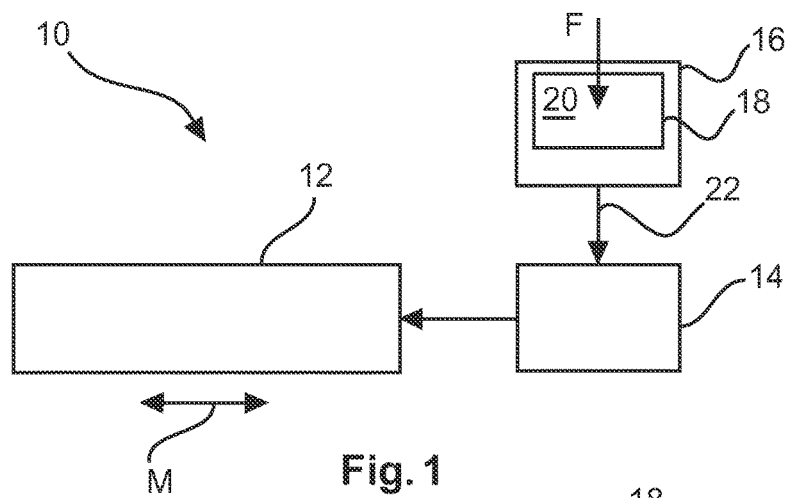
FIG. 1 shows an example of a schematic setup of a driving device for moving equipment.

FIG. 1 shows a driving device 10 for moving equipment, comprising a motor-driven positioning unit 12, a central processing unit 14, and a user interface 16 with at least one sensor unit 18. The motor-driven positioning unit is configured to carry out a movement of movable equipment, indicated with double arrow M. It must be noted that the movement may take place in different directions on a surface or in a plane, or in 3D space. The central processing unit 14 is configured to control the movement of the equipment provided by the motor-driven positioning unit 12. The at least one sensor unit 18 comprises at least one touch sensitive area 20. The at least one sensor unit 18 is configured to provide control signals 22 to the central processing unit 14 in dependency from a pressure, i.e. force F applied by a user to the at least one touch sensitive area 20. The at least one sensor unit 18 is configured to be fixedly attached to the movable equipment.

For example, the equipment is provided with the movement direction-positioning unit 12, and the central processing unit 14 is also integrated with the equipment. Further, the user interface 16 is also provided directly on the equipment. Thus, all the above-mentioned units move together with the movable equipment.

Figure 2A:
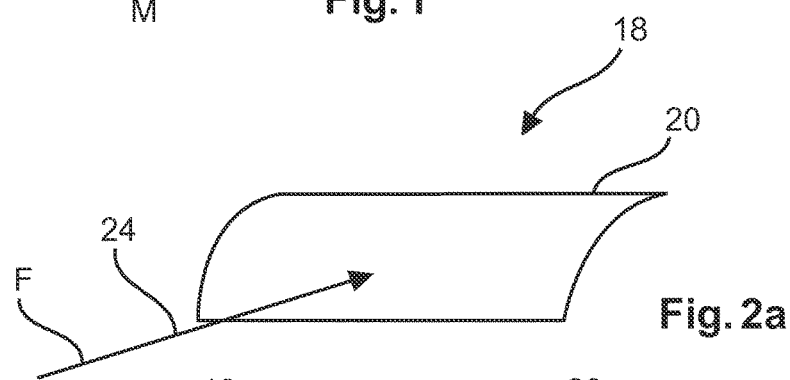
FIG. 2 shows an example of a touch sensitive area as a user interface in a perspective illustration in FIG. 2A, and in top views in FIG. 2B, FIG. 2C, and FIG. 2D.
Figure 2B:
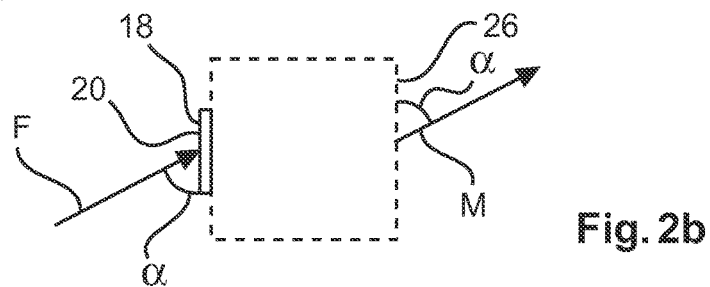

FIG. 2A shows the touch sensitive area 20 of the sensor unit 18 in a perspective view. For example, the touch sensitive area 20 is provided as a curved edge surface. Further, a straight arrow 24 indicates the force F applied by the user. The sensor is configured to provide control signals in dependency from the pressure force. In addition, or alternatively, the sensor is configured to provide control signals in dependency from a pressure acting direction.

Figure 2C:
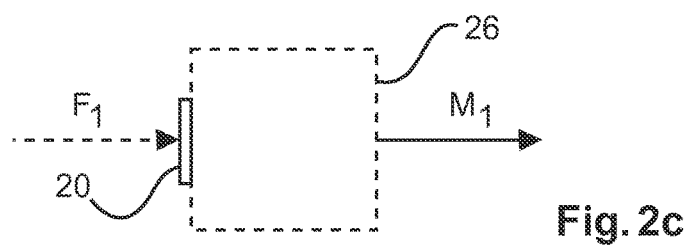
Figure 2D:
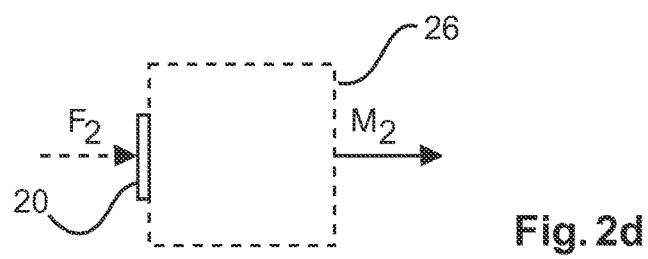

As can be seen in FIG. 2A, the sensor unit 18 is shown, for example in a top view. Further, a dashed rectangle 26 indicates movable equipment that is to be moved by the movement direction-positioning unit 12 (not further shown). The pressure or force F acts in a certain acting direction, for example with an angle α in relation to the touch sensitive area 20 of the sensor unit 18. An arrow M indicates the resulting movement with a direction in dependency from the direction of the pressure F. For example, the moving direction also has an angle of α with respect to the movable equipment, i.e. the dashed rectangular 26. Of course, in case of an inclined surface of the movable equipment, a different angle would be provided in order to align the pressure force direction and the moving direction. FIG. 2C shows in a similar illustration a pressure force F1 acting on the touch sensitive area 20. Thus, a resulting movement M1 is indicated with a further arrow. In case the pressure force F1 is rather large, as schematically indicated by the length of the arrow F1, a large movement, also indicated with rather large length of the arrow M1, is achieved. FIG. 2D shows a further similar illustration, where a smaller pressure force F2 results in a smaller movement M2.

For example, the touch sensitive area 20 is configured to be arranged on the movable equipment such that the pressure force is executable by a user in an acting direction touching the touch sensitive area, which acting direction is in concordance with an intended moving direction, as illustrated above.

Figure 3:
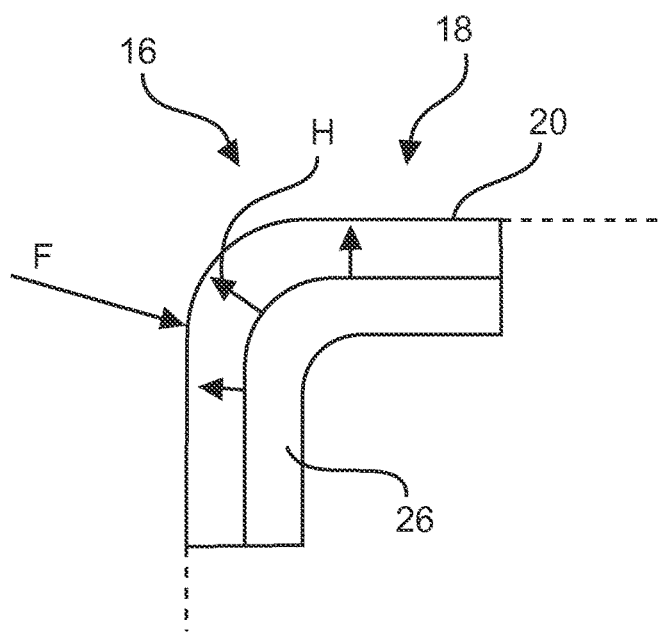
FIG. 3 shows an example of a touch sensitive area in a cross-section.

FIG. 3 shows a cross-section through a touch sensitive area 20 of the at least one sensor unit 18 of the user interface 16. The user interface 16 comprises a haptic feedback unit 26, which is configured to provide a haptic signal, indicated with smaller arrows H, to the user while the user is in touching contact with the sensor unit, which touching contact is indicated with an arrow F indicating the force applied by the user. The user senses H through the outer sensor layer.

For example, the touch sensitive area 20 comprises an electroactive polymer, for example an elastomer with two spaced apart layers of electrodes. As indicated, the feedback unit 26 is provided underneath such that haptic signals are provided through the touch sensitive area 20.

To protect the electrodes from external noise sources or capacitance, the detection electrodes within the sensor can be encapsulated between two extra layers of electrodes both at mass potential.

In a further example, not further shown, the touch sensitive area 20 is provided as a dielectric elastomer with two layers of electrodes. In a first operating mode, a (pressure) force acting on the deformable sensor is detected. In a second mode, a driving voltage is applied to the sensor in order to cause a movement or change of the deformable material. The first and second modes of operation are provided alternately such that the user has the feeling of an actively moving or changing sensor surface.

Figure 4:
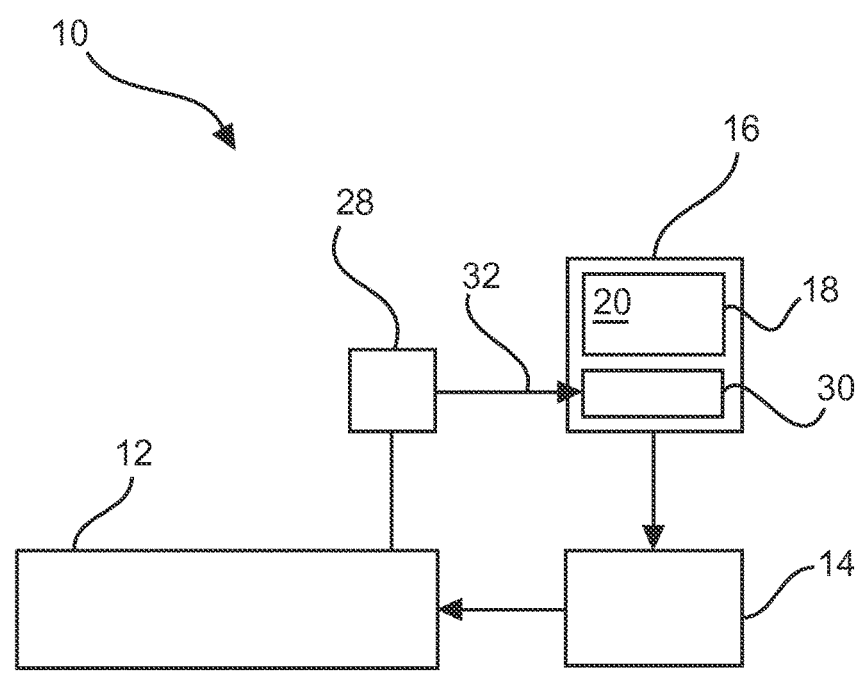
FIG. 4 shows a further example of a driving device in a schematic setup.

FIG. 4 shows a further example of a driving device 10 in a schematic setup. A collision control unit 28 is provided to detect an upcoming collision of the movable component. A feedback is provided as a haptic warning signal via the touch sensitive area 20. For example, a haptic feedback unit 30 is provided, for example as described above. An arrow 32 indicates a respective collision signal provided by the collision control unit 28. In a further example, the collision control unit 28 is provided with a communication with the processing unit 14, which then provides a respective control signal to the haptic feedback unit 30.

For example, the equipment to be moved is a medical apparatus. The motor-driven positioning unit 12 is then configured to carry out a movement of the medical equipment in an examination room.

According to a further example (not further shown), a confirmation unit is provided to enable and/or block an unwanted operation of the motor-driven positioning unit.

Figure 5:
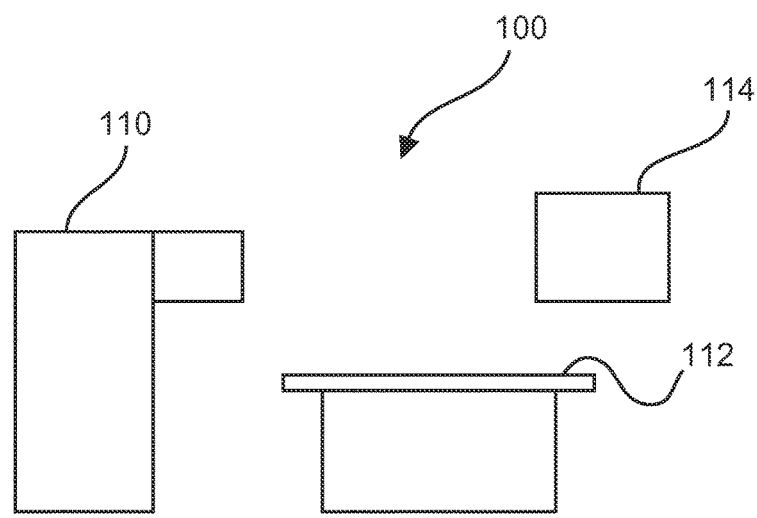
FIG. 5 shows an example of a medical examination system in a schematic setup.

FIG. 5 shows a medical examination system 100 comprising at least one movable medical equipment. Such movable medical equipment may comprise an imaging apparatus 110, a patient support 112, or a display 114. At least one of the medical equipment comprises a movable support and is provided with a driving device according to one of the above-mentioned examples. The at least one sensor is attached to the movable medical equipment (not further shown).

Figure 6:
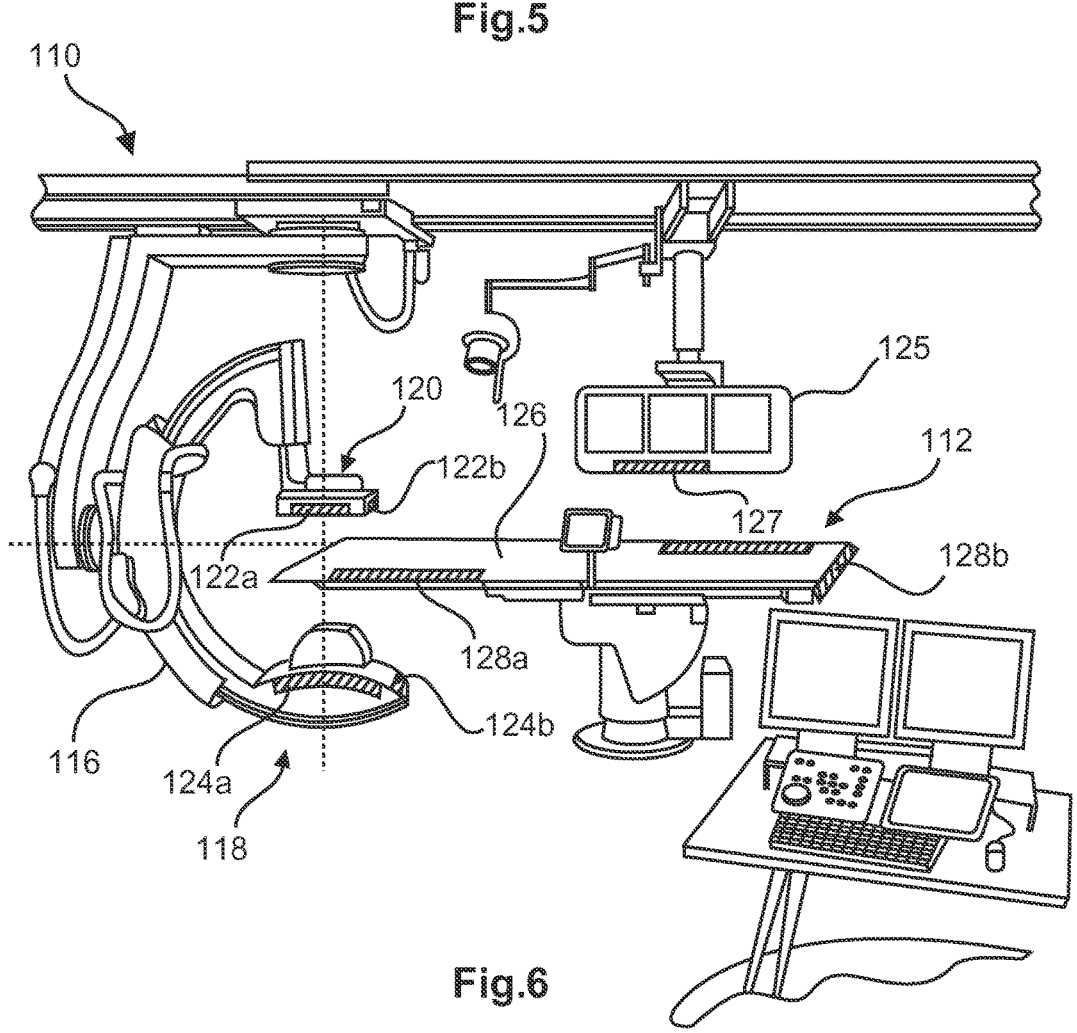
FIG. 6 shows a further example of a medical examination system in form of a C-arm arrangement in a perspective illustration.

FIG. 6 shows the imaging apparatus 110 in form of a C-arm arrangement 116 of a C-arm X-ray imaging system. The C-arm system comprises an X-ray source 118 and an X-ray detector 120. Sensor surfaces 122 are provided at least on two sides of the X-ray detector 120, which sensor surfaces are indicated with reference numeral 122*a* and 122*b*. In a further example, more than two sensor surfaces are provided. In another example, two sensor surfaces are arranged on opposite sides of the detector housing or detector support structure. Further, sensor surfaces 124 may also be provided alternatively or in addition at least on two sides of the X-ray source 118, which sensor surfaces are indicated with reference numeral 124*a* and 124*b*. The motor-driven positioning unit provides the movement of the equipment.

Instead of a C-arm system, also other medical imaging arrangements are provided with movable equipment, such as other types of X-ray imaging systems or ultrasound imaging systems.

In a further example, which is also shown in FIG. 6, but which does not mean a necessary combination of the two examples, the patient support is a patient table 126. Sensor surfaces 128 are provided at least on two sides of the patient table, as indicated with reference numeral 128*a* and 128*b*. The motor-driven positioning unit provides the movement of the equipment.

In a still further example, which is also shown in FIG. 6, but which does also not mean a necessary combination of the two examples, a monitor arrangement 125 is provided with at least one sensor surface 127. The motor-driven positioning unit provides the movement of the equipment.

It must be noted that instead of providing sensor surfaces on two sides of an equipment to be moved, sensor surfaces may be provided along more, or even on all sides. Further, in case of two sides, the sensor surfaces may be provided on opposing sides, or on adjacent sides.

For example, the sensor surfaces are provided along the edges. The sensor surfaces may be provided on handles or grips for moving the equipment (not further shown). In a further example, also not further shown, large surfaces are provided as sensor surfaces on the movable medical equipment. The term "large surfaces" relates to, for example, a length that is at least half way along an edge of the medical equipment, or a length of at least 30 cm, or a surface area of at least 20 cm×20 cm. The term "large" relates to a surface area that is at least large enough such that a user has enough sensor surface area to be touched by one hand without having to be careful to match the surface area when touching the sensor. Thus, a facilitated way of operating the movement of the equipment is provided, thus requiring only very little attention for the operation. Hence, the user, for example a surgeon, is distracted in a minimum way only.

Figure 7A:
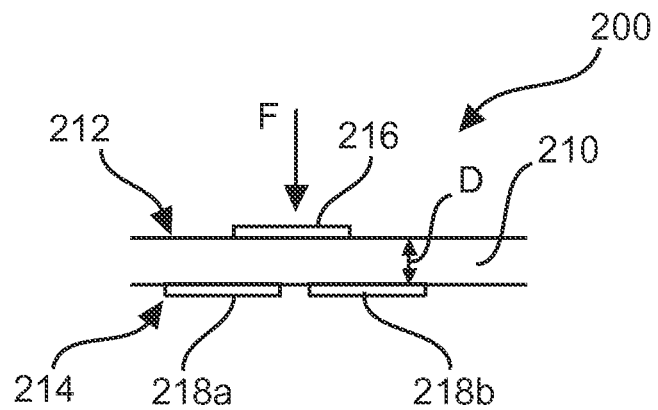
FIG. 7 shows a sensor of a touch sensitive area for detecting a direction of an actuating force in a schematic cross-section in FIG. 7A, and a top view in FIG. 7B.
Figure 7B:
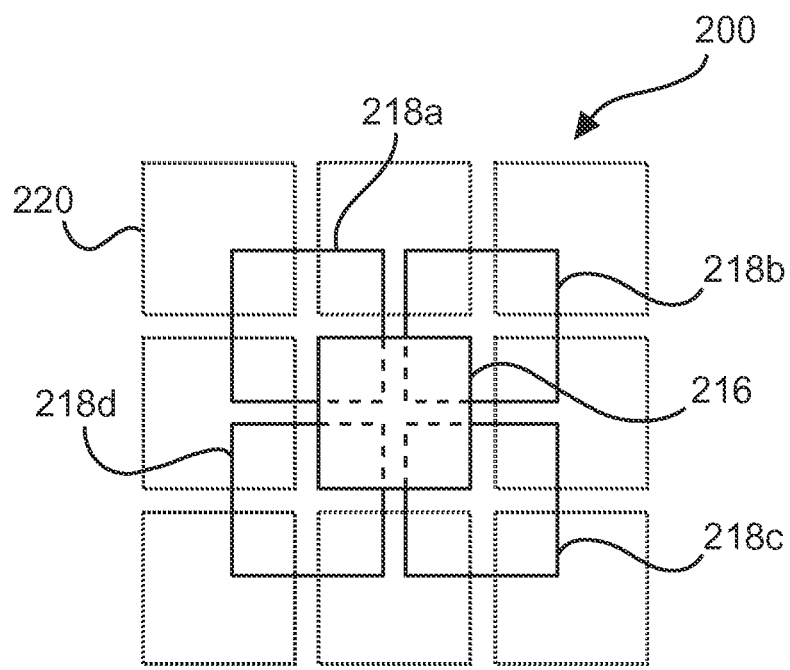

FIG. 7 shows a sensor 200 of a touch sensitive area for detecting a direction of an actuating force, e.g. pressing force, in a schematic cross-section in FIG. 7A and a top view in FIG. 7B. The sensor 200 comprises a dielectric elastomer 210 and a first layer of electrodes 212 and a second layer of electrodes 214. The first and the second layers 212, 214 of electrodes are spaced apart by the dielectric elastomer 220 in a variable distance D according to a pressure force F acting on the sensor 200. One of the first or second layers of electrodes comprises at least one electrode 216 that at least partly overlaps with at least two electrodes 218*a* and 218*b* of the other one of the second or first layer of electrodes. For example, the upper, i.e. first layer of electrodes is provided with one electrode, i.e. the electrode 216 that overlaps with the electrodes on the lower, i.e. second layer of electrodes 214. Thus, a local change of capacity provides information about strain and direction on an acting pressure force. For example, in case the pressure force acting in an inclined direction, i.e. different than the perpendicular acting force F shown in FIG. 7A, the electrode 216 would be provided in an inclined manner also, such that a distance D between the electrode 216 and the electrode 218a would be different to the distance D between the electrode 216 and the electrode 218b.

FIG. 7B shows a situation where the electrode 216 overlaps with four electrodes 218a, 218b, 218c, and 218d. Further, additional electrodes of the first layer of the electrode 216 are indicated with dashed lines 220.

Figure 10:
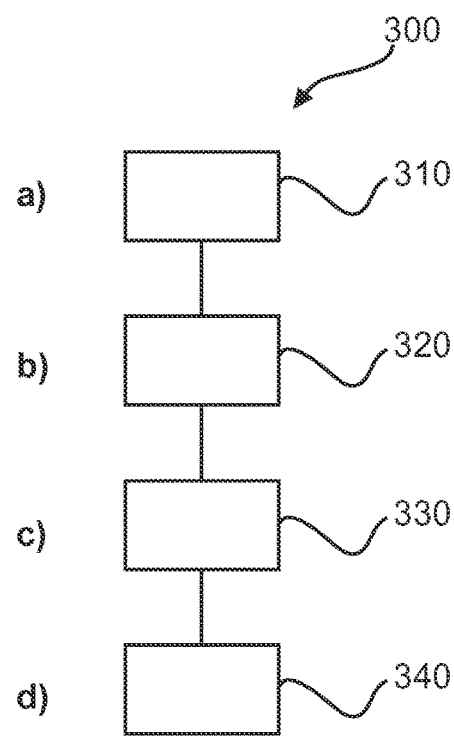
FIG. 10 shows basic steps of an example of a method for moving equipment.

FIG. 10 shows a method 300 for moving equipment that comprises the following steps: In a first step 310, a touch sensitive area of a sensor unit of a user interface is touched, which sensor unit is attached to a movable equipment. In a second step 320, a control signal is generated in dependency from a pressure applied by a user to the at least one touch sensitive area. In a third step 330, the generated control signal is provided to a central processing unit. In a fourth step 340, a motor-driven positioning unit is actuated based on the control signal. The first step 310 is also referred to as step a), the second step as step b), the third step as step c), and the fourth step as step d).

Figure 11:
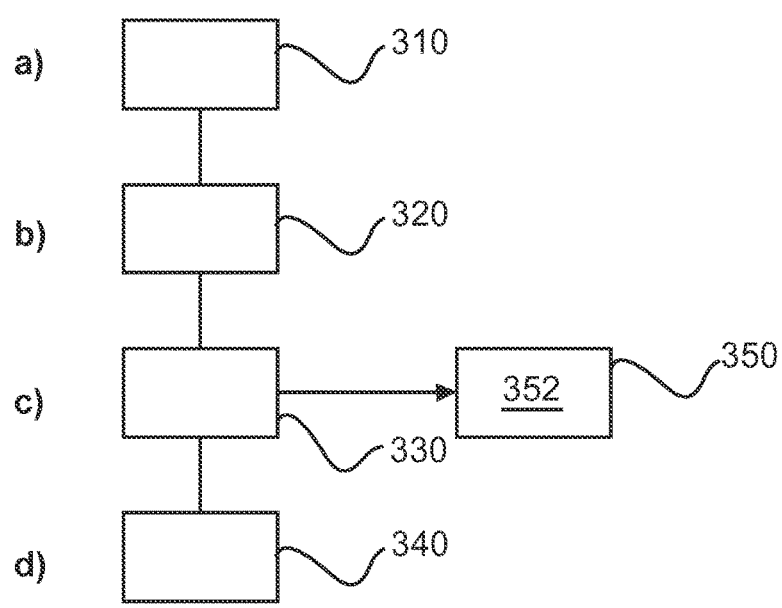
FIG. 11 shows a further example of a method for moving equipment.

FIG. 11 shows a further example, where a further step 350 is provided, in which a haptic signal 352 is provided to the user while in touching contact with the sensor unit. The haptic signal 352 is provided, for example, as a different degree of softness in dependency of the weight of the equipment to be moved.

Figure 8:
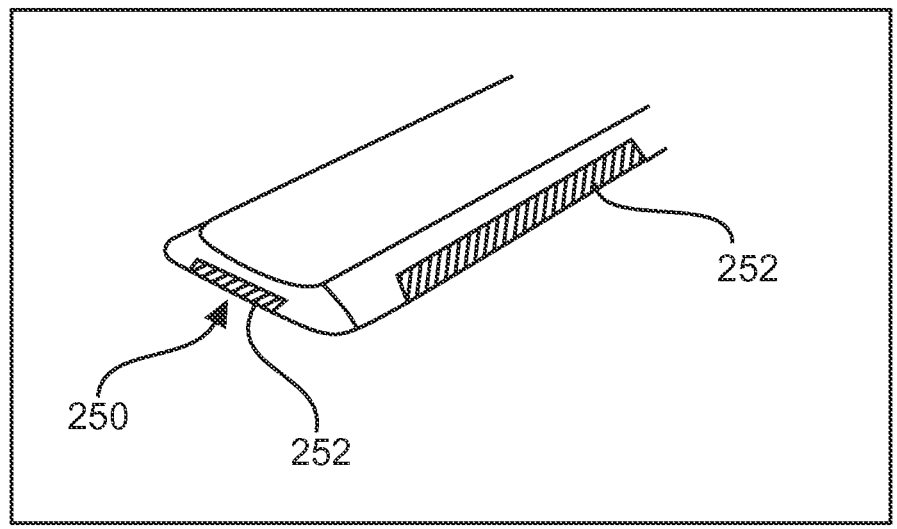
FIG. 8 shows an example of a patient table with a sensor surface.

FIG. 8 shows a patient table 250 with two sensor surfaces 252, marked with a line pattern, along a length of an edge of the patient table 250.

Figure 9:
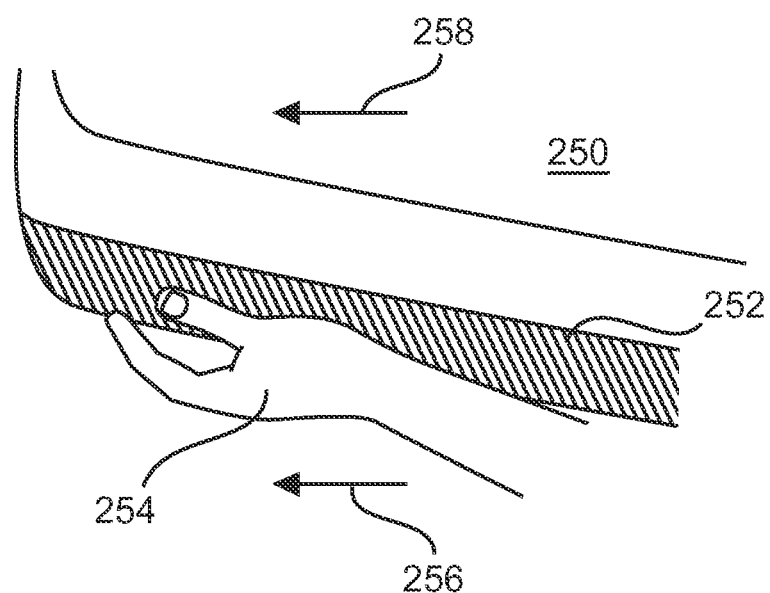
FIG. 9 shows a user's hand applying a pressure, i.e. actuating force.

FIG. 9 shows a user's hand 254, providing a pressure force in a pushing direction 256, resulting in a movement direction 258 of the patient table 250. By the user's hand 254, the sensor material of the sensor surface 252 is (slightly) deformed.

In a further example, several sensors are fixed to the sides of the patient table. This provides an intuitive way for the user to move the equipment. The sensor may be made of a deformable and flexible material and can be placed on any curved shape, for example. The sensor may be connected to a patient positioning system of the patient table, which also may comprise a positioning of the table in relation to the X-ray tube and the detector, i.e. the X-ray tube and detector may also be provided with respective movement equipment in order to achieve the relative movement. The sensor will then follow the hand of the operator, for example after a touch confirmation. Next, the operator may confirm the position with his hand, and the sensor may be disabled to prevent any unexpected or unwanted movements.

In a further example, sensor surfaces are provided to lighting equipment or monitoring equipment that are movably supported.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A driving device for moving equipment, comprising:
   a motor-driven positioning unit;
   a central processing unit; and a user interface with at least one sensor unit;
wherein the motor-driven positioning unit is configured to carry out a movement of a movable equipment;
wherein the central processing unit is configured to control the movement of the equipment provided by the motor-driven positioning unit;
wherein the at least one sensor unit comprises at least one touch sensitive area arranged on the movable equipment such that a force is executable by a user in an acting direction when touching the touch sensitive area, which acting direction is in concordance with an intended moving direction,
wherein the touch sensitive area is a deformable capacitive sensor arranged to detect and provide information about strain and direction of the force, wherein a surface of the touch sensitive area is deformable and the detected force comprises a compressive force and a shear force,
wherein the at least one sensor unit is configured to provide control signals to the central processing unit in dependency from the detected force; and
wherein the at least one sensor unit is configured to be fixedly attached to the movable equipment.

2. Driving device according to claim 1, wherein the sensor unit is configured to provide control signals in dependency from at least one of the group of:
  i) pressure force; and
  ii) pressure acting direction.

3. Driving device according to claim 1, wherein the sensor unit is configured to provide a movement control signal with movement vector components corresponding to vector components of the force.

4. Driving device according to claim 1, wherein the user interface comprises a haptic feedback unit, which is configured to provide a haptic signal to the user while the user is in touching contact with the sensor unit.

5. Driving device according to claim 1, wherein a collision control unit is provided to detect an upcoming collision of the movable component; and wherein a feedback is provided as a haptic warning signal via the touch sensitive area.

6. Driving device according to claim 1, wherein the equipment is a medical apparatus, and the motor-driven positioning unit is configured to carry out a movement of the medical equipment in an examination room.

7. A medical examination system, comprising at least one movable medical equipment of the group of:
  an imaging apparatus;
  a patient support; and
  a display;
  wherein at least one of the medical equipment comprises a movable support and is provided with a driving device according to claim 1; and
  wherein the at least one sensor is attached to the movable medical equipment.

8. Medical examination system according to claim 7; wherein the imaging apparatus is a C-arm arrangement of a C-arm X-ray imaging system; and wherein sensor surfaces are provided at least on two sides of the X-ray detector or X-ray source.

9. Medical examination system according to claim 7; wherein the patient support is a patient table; and wherein sensor surfaces are provided at least on two sides of the patient table.

10. Medical examination system according to claim 7, wherein the sensor surfaces are provided as large surfaces on the movable medical equipment; wherein the large surfaces are provided with at least one of the group of:
  a length that is at least half way along an edge of the medical equipment;
  a length of at least 30 cm; and
  a surface area of at least 20 cm×20 cm.

11. The medical examination system of claim 7, wherein the touch sensitive area comprises a curved edge surface attached to the movable medical equipment.

12. A computer program element for controlling an apparatus according to claim 1.

13. A computer readable medium having stored the program element of claim 12.

14. The driving device of claim 1, wherein the touch sensitive area comprises a curved edge surface.

15. A sensor of a touch sensitive area for detecting a direction of an actuating force, comprising:
  a first and a second layer of electrodes;
  a dielectric elastomer;
  a deformable surface;
  wherein the first and the second layer are spaced apart by the dielectric elastomer in a variable distance according to a pressure force acting on the sensor;
  wherein one of the first or second layer of electrodes comprises at least one electrode that at least partly overlaps with at least two electrodes of the other one of the second or first layer of electrodes;
  wherein a local change of capacity detects and provides information about strain and direction of an acting force;
  wherein the direction of the acting force is in concordance with an intended moving direction of movable equipment fixedly attached to the sensor; and
  wherein the detected force comprises a compressive force and a shear force.

16. The sensor of claim 15, wherein a direction of the acting force is determined from a difference between a distance between a first electrode of the at least two electrodes of the second layer and the electrode of the first layer and a distance between a second electrode of the at least two electrodes of the second layer and the electrode of the first layer.

17. A method for moving equipment, comprising the following steps:
  a) touching a deformable capacitive sensor of a sensor unit of a user interface, which sensor unit is attached to a movable equipment;
  b) generating a control signal in dependency from a detected strain and direction of a force applied by a user to the at least one touch sensitive area, wherein the detected force comprises a compressive force and a shear force;
  c) providing the generated control signal to a central processing unit; and
  d) actuating a motor-driven positioning unit based on the control signal.

18. The method of claim 17, wherein the sensor unit comprises a curved edge surface attached to the movable medical equipment.

* * * * *